United States Patent [19]

Schweighardt et al.

[11] Patent Number: 4,881,682
[45] Date of Patent: Nov. 21, 1989

[54] VAPOR PHASE SOLDERING WITH PERFLUORINATED BUTYL DERIVATIVE COMPOUNDS

[75] Inventors: Frank K. Schweighardt, Allentown; Webb I. Bailey, Fogelsville, both of Pa.

[73] Assignee: Air Products and Chemicals, Inc., Allentown, Pa.

[21] Appl. No.: 203,401

[22] Filed: Jun. 6, 1988

Related U.S. Application Data

[62] Division of Ser. No. 89,475, Aug. 25, 1987, Pat. No. 4,777,304.

[51] Int. Cl.$^4$ .......................... B23K 3/00; C07C 19/08
[52] U.S. Cl. .................................. 228/242; 228/180.1; 570/130
[58] Field of Search .......................... 427/96; 570/130; 228/242, 180.1

[56] References Cited

U.S. PATENT DOCUMENTS

| | | | |
|---|---|---|---|
| Re. 30,399 | 9/1980 | Ammann et al. | 228/180 |
| 2,487,820 | 11/1949 | McBee et al. | 260/648 |
| 2,631,170 | 3/1953 | Fowler | 260/648 |
| 3,775,489 | 11/1973 | Margrave et al. | 260/648 |
| 3,786,324 | 1/1974 | Kotschy | 317/258 |
| 4,106,557 | 8/1978 | Sonobe et al. | 165/105 |
| 4,143,079 | 3/1979 | Moore | 260/648 |
| 4,396,785 | 8/1983 | Kobayashi et al. | 570/129 |
| 4,453,028 | 6/1984 | Lagow | 570/130 |
| 4,549,686 | 10/1986 | Sargent et al. | 228/242 |

FOREIGN PATENT DOCUMENTS

0194009 9/1986 European Pat. Off. .
785641 10/1957 United Kingdom .
2110204 6/1963 United Kingdom .
1281822 7/1972 United Kingdom .

OTHER PUBLICATIONS

*Organic Fluorides Part V Fluorination of Hydrocarbons with Cobalt Trifluoride* R. N. Haszeldine and R. Smith, Journal of Chemistry Society (1950).

"Ternary Systems of Liquid Sulfur Dioxide"—Alfred W. Francis, Journal of Chemical and Engineering Data, vol. 10, No. 1 (Jan. 1965).

"Ternary Systems of Sulfur and Sulfur Compounds"—Alfred W. Francis, Journal of Chemical and Engineering Data, vol. 11, No. 4 (Oct. 1966).

*Primary Examiner*—Donald B. Moyer
*Assistant Examiner*—Tracy A. Hanna
*Attorney, Agent, or Firm*—Geoffrey L. Chase; James C. Simmons; William F. Marsh

[57] ABSTRACT

Novel compositions of matter are disclosed having the formula:

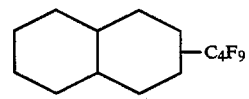

wherein the carbon rings are fully fluorinated to remove all hydrogens and olefinic character. The compositions have utility as heat transfer agents, hydraulic fluids, vapor phase soldering fluids, gas ($O_2$, $N_2$, $CO_2$, $H_2$, etc.) transport agents, such as in biological and medical fields, as well as utility as burn-in test fluid.

11 Claims, No Drawings

VAPOR PHASE SOLDERING WITH PERFLUORINATED BUTYL DERIVATIVE COMPOUNDS

This is a division of application Ser. No. 89,475 filed Aug. 25, 1987, now U.S. Pat. No. 4,777,304.

TECHNICAL FIELD

The present invention is related to the field of perfluorinated alkyl substituted condensed ring compounds. More specifically, the present invention is directed to various butyl derivatives of decahydronaphthalene (decalin) prepared from naphthalene, which former compound is then fully fluorinated.

BACKGROUND OF THE PRIOR ART

Fluorinated carbon compounds are finding increasing utility in modern industry, such as the electronics fabrication industry, and researchers have found heightened interest in fluorinated compounds for various biological and medical applications, such as synthetic blood and diagnostic fluids.

Perfluorinated multiple condensed ring compounds have been known for a significant period of time, such as perfluorophenanthrene as disclosed in U.S. Pat. No. 2,487,820. That patent makes a broad, general and unsupported disclosure that:

"Fused-ring aromatic hydrocarbons such as anthracene, naphthalene, phenanthrene and their substitution derivatives, can be fluorinated readily with the addition of fluorine atoms at the points of unsaturation and, if desired, with the replacement of hydrogen in the molecule, and the production of saturated fluorine-containing compounds."

Partially fluorinated compounds are exemplified by the 1-methyl-(3,3,3-trifluoropropyl) naphthalene compounds disclosed in U.S. Pat. No. 4,396,785. These compounds are only marginally fluorinated and the condensed carbon rings retain their unsaturated aromatic character.

The tertiary butyl derivatives of a single carbon ring, cyclohexane, is disclosed in U.S. Pat. No. 4,453,028.

Perfluoro-2-methyldecahydronaphthalene has been reported to have been synthesized from 2-methyl naphthalene using cobalt trifluoride fluorination technology as set forth in article titled, *Organic Fluorides. Part V. Fluorination of Hydrocarbons With Cobalt Trifluoride* by R. N. Haszeldine and F. Smith appearing in Journal of Chemistry Society (1950) pages 3617 to 3623.

The cobalt trifluoride fluorination of 1-methyl decalin to produce perfluoro-1-methyl decalin has also been set forth in British Patent No. 1,281,822. Fluorination of substituted naphthalenes is generally disclosed.

The basic technique for cobalt trifluoride fluorination is set forth in U.S. Pat. No. 2,631,170.

U.S. Pat. No. 3,775,489 is directed to the fluorination of various aromatic carbon compounds of the naphthalene and anthracene class.

U.S. Pat. No. 3,786,324 discloses a utility for perfluorinated hydrocarbons comprising dielectric fluids for capacitors. The compound 1-trifluoromethyl perfluorodecalin is mentioned as a potential dielectric fluid.

U.S. Pat. No. 4,106,557 describes a refrigeration apparatus utilizing various halogenated carbon refrigerants, including cyclic fluorinated carbon ethers.

U.S. Pat. No. 4,143,079 discloses perfluorinated 1-methyl-4-isopropyl cyclohexane. This material is recited to have utility as an artificial blood component.

U.S. Pat. No. Re. 30,399 discloses a technique for soldering electronic components in a mass production mode in the heated vapor of a boiling fluid wherein the vapor condenses on cold solder to be reflowed and the solder is melted by the heat of vaporization evolved during the condensation of the adhering fluid vapor. This form of soldering is known as vapor phase soldering, condensation soldering and various reflow soldering nomenclatures. The criteria delineated for a heat transfer liquid for such soldering includes: a boiling point above the melting point of the solder wherein the boiling point is preferably sharply defined and dependent upon a single component rather than multicomponent materials, electrically non-conducting characteristics, vapors which are non-oxidizing, chemically stable and inert, non-toxic, non-inflammable and relatively denser than air, relatively high latent heat of vaporization, and degreasing properties. Fluorinated polyoxypropylene is a disclosed fluorocarbon suitable for heat transfer liquid choice.

U.S. Pat. No. 4,549,686 describes vapor phase soldering using perfluorotetradecahydrophenanthrene (perfluorophenanthrene).

British Patent No. 785,641 discloses the fluorination of various carbon compounds with hydrogen fluoride wherein such compounds include benzene, toluene, anthracene and diamylnaphthalene. Retene, which is 1-methyl-7-isopropyl phenanthrene, is also capable of the recited fluorination treatment.

U.K. Patent Application No. 2110204A discloses various perfluoroalkyl cyclohexane mixtures useful for vapor phase soldering in the boiling range of 180° to 300° C. These materials are produced by the fluorination of narrow cut linear alkylbenzene compounds with cobalt trifluoride.

European Patent Application No. 0 194 009 discloses fluorochemical compositions comprising compounds in the form of perfluoropolycycloalkane ring assemblies having (a) at least two perfluorinated cyclohexane rings, (b) at least two perfluorinated fused ring systems, or (c) a combination of at least one perfluorinated fused ring system with at least one perfluorinated cyclohexane ring, each perfluorinated ring or ring system being directly joined to another perfluorinated ring or fused ring system by a single bond. The rings may have certain substituent groups.

The prior art fluorination compounds have failed to provide a stable inert perfluoro compound having a desirable sharp boiling point in the approximate range of 215° C. which is most desirable for presently existing vapor phase soldering utilities. In addition, the prior art compounds suffer from various levels of susceptibility to heat degradation to hydrogen fluoride and perfluoroisobutylene, as well as having undesirable fluorine utilizations due to significant levels of aliphatic character. The present invention overcomes these shortcomings.

BRIEF SUMMARY OF THE INVENTION

The present invention is a perfluorinated compound of the formula:

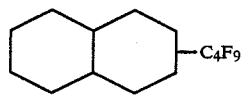

wherein the carbon rings are fully fluorinated.

Preferably, the butyl radical constitutes normal butyl, secondary butyl, tertiary butyl, or isobutyl. Preferably, these butyl derivatives are positioned in the number 2 position on the decalin ring.

The present invention is also directed to a method of soldering wherein a component to be soldered is immersed in a vapor bath to melt the solder, and the component is then withdrawn from the vapor bath, the improvement comprising that the vapor bath is composed substantially of compounds of the formula:

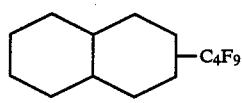

wherein the carbon rings are fully fluorinated.

The vapor bath can comprise mixtures of the recited compounds with other compounds such as perfluorophenanthrene.

DETAILED DESCRIPTION OF THE INVENTION

The perfluorobutyldecalin compounds of the present invention have an empirical formula of $C_{14}F_{26}$ and a molecular weight of 662. The materials are liquid at room temperature and exhibit boiling points in the approximate range of 210°–216° C. After synthesizing these compounds from their hydrocarbon precursors the perfluoro products produced from cobalt trifluoride fluorination have been confirmed by $^{19}F$ NMR (nuclear magnetic resonance) and GC/MS (gas chromatography mass spectroscopy). These compounds exhibit excellent utility as vapor phase soldering fluids due to their sharp boiling points, their degreasing properties, their lack of flammability, their low toxicity, their low thermal degradation, particularly into hydrogen fluoride and perfluoro isobutylene byproducts, their extremely low electrical conductivity, their non-oxidizing characteristics, as well as the trait of their vapor being relatively denser then air. In addition to vapor phase soldering fluid utility, the compounds of the present invention exhibit low fluorine utilization on a relative scale when being synthesized from the hydrocarbon precursors, such that the cost of fluorination is relatively minimal in comparison to alternative compounds. The compounds also have applicability as general heat transfer fluids without regard to whether they are vaporized or not, such as cooling fluids for capacitors, transformers and radar equipment, as well as utility as hydraulic pump fluid. The compounds of the present invention also exhibit oxygen transport characteristics, such as to indicate their applicability for biological and medical utilities as artifical blood and perfusion agents.

The feedstocks for the compounds of the present invention are hydrocarbon liquids such as n-butylnaphthalene, secondary-butylnaphthalene, tertiary-butyl naphthalene and isobutylnaphthalene, all of which are prepared by the known alkylation of naphthalene. The new compositions of matter reported herein are substantially the perfluorinated analogs of the hydrocarbon starting materials, wherein all aromatic character, unsaturation and hydrogen is removed from the perfluorinated products. All stereo isomers and conformers of n-butylnaphthalene, secondary-butylnaphthalene, tertiary-butylnaphthalene and isobutylnaphthalene are represented by this invention. For the sake of clarity, the numbering of the ring carbons on the decalin ring (fully saturated naphthalene derivative) are set forth below:

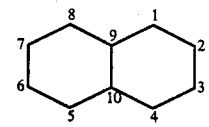

The preparations for the new fluorochemicals are set forth in Examples 1 through 7 below. The perfluorochemicals produced here have been shown by IR (infrared) and UV (ultraviolet) spectroscopy to be at the limits of detection for residual hydrogen and olefin character, respectively. These low values are possible by the addition of a direct fluorination cleanup step subsequent to the cobalt trifluoride initial fluorination step performed at elevated temperatures as detailed in Examples 2 and 5 below.

EXAMPLE 1

Notebook 7826-9249-22,23

5 grams of n-butylnaphthalene were charged to a 75 ml stainless steel sample cylinder. The cylinder was gradually heated to the boiling point of n-butylnaphthalene (288° C.) while purging with 20 cubic centimeters per minute of nitrogen. The n-butylnaphthalene/nitrogen gas stream was fed into a heated stainless steel tubular reactor 1" in diameter and 21" long containing approximately 100 grams cobalt trifluoride. The reactor was held at approximately 275° C. The n-butylnaphthalene feed was subsequently converted to a perfluorochemical in the reactor and collected in a trap held at 25° C. 6.05 grams of a light yellow liquid was collected. Additional material was produced under identical reactor conditions.

EXAMPLE 2

Notebook 7826-9249-33

24.44 grams of the combined cobalt trifluoride products of Example 1 were charged to a 40 ml stainless steel sample cylinder for a direct fluorination/clean-up step. A fluorine/nitrogen gas mixture increasing to 100% fluorine with time was sparged into the liquid at 25° C. and 100° C. Approximately 3.0 grams of elemental fluorine was added into the crude perfluorochemical mixture. A 1.5 gram weight loss was observed.

EXAMPLE 3

Notebook 7826-9249-34

21.38 grams of the directly fluorinated product of Example 2 was distilled in a micro spinning band still. A fraction boiling at 214° C. was collected which represented 31% of the original charge. The fluorochemical was identified as perfluoro, n-butyldecalin. Analytical information is shown in Table 1 below.

TABLE 1

| | $NMR-^{19}F$[a] | | |
|---|---|---|---|
| | $CF_3$ | $CF_2$ | $CF$ |
| | −66 to −83[b] multiplet | −101 to 131[b] multiplet | −172 to 188[b] multiplet |
| | Relative F atomic ratio | | |
| calculated | 1.0 | 6.6 | 1.0 |
| observed | 1.0 | 5.3 | 1.1 |
| | MASS SPECTRUM (m/e)[c] | | |
| calculated | | | 662 ($C_{14}F_{26}$) |
| observed | | | 662 ($C_{14}F_{26}$) |

[a] in $CDCl_3/C_2Cl_3F_3$
[b] ppm from $CCl_3F$
[c] electron ionization and/or chemical ionization with $CH_4$

EXAMPLE 4

Notebook 7826-8876-94

Twenty-five grams of secondary-butylnaphthalene was charged to a sample cylinder and connected to an enclosed hot plate operating at 300° C. The secondary-butylnapthalene was fed onto the hot plate by a metering pump at a rate of 9.3 grams per hour, into a 15.5 cc/min. nitrogen stream. The organic/nitrogen steam was carried into a cobalt trifluoride reactor 10 centimeters in diameter and 60 centimeters long containing approximately 3,000 grams of cobalt trifluoride. The reactor was heated with a three zone furnace operating at 300° C. and 330° C., respectively. The secondary-butylnaphthalene feed was subsequently converted to a perfluorochemical in the reactor, and was collected in a trap held at 25° C. 44.2 grams of a light yellow liquid was collected. Additional material was produced under similar reactor conditions.

EXAMPLE 5

Notebook 7826-8490-63

101 grams of the combined cobalt trifluoride products of Example 4 were charged to a 40 milliliter stainless steel sample cylinder for a direct fluorination cleanup step. A fluorine/nitrogen gas mixture increasing to 100% fluorine with time, was sparged into the liquid at 25° C. and 150° C. Approximately 1 gram of elemental fluorine was added into the crude perfluoro chemical mixture.

EXAMPLE 6

Notebook 7826-8490-65

28.6 grams of the directly fluorinated product of Example 5 was distilled in a micro spinning band still. A fraction boiling at 214° C. was collected which represented 27.3% of the original charge. The fluorochemical was identified as perfluoro, secondary-butyldecalin by GC/MS (m/e 643=$C_{14}F_{26}$-F).

EXAMPLE 7

Notebook 7826-8490-59

4.4 grams of tertiary-butylaphthalene were charged to a 75 milliliter stainless steel sample cylinder. The cylinder was gradually heated to the boiling point of tertiary-butylnaphthalene while purging with 20 cubic centimeters per minute of nitrogen. the tertiary-butylnaphthalene/nitrogen gas stream was fed into a heated stainless steel tubular reactor, 1 inch in diameter and 21 inches long, containing approximately 100 grams of cobalt trifluoride. The reactor was held constant at 275° C. The tertiary-butyl naphthalene feed was subsequently converted to a perfluorochemical in the reactor and was collected in a trap held at 25° C. 4.7 grams of a light yellow liquid was collected. The presence of perfluoro, tertiary-butyldecalin was confirmed by GC/MS (m/e 662×$C_{14}F_{26}$-F).

EXAMPLE 8

Notebook 7826-8490-102

A glass vapor phase soldering apparatus consisting of a 100 ml flask connected to a condenser was used to demonstrate vapor phase soldering with perfluoro, secondary-butyldecalin. A solder paste consisting of 96.5% tin and 3.5% silver was used to coat a printed circuit board. A surface mount device was positioned on the solder paste and the entire assembly was immersed in perfluoro, secondary-butyldecalin which had been heated to reflux temperature. Solder reflow was observed to occur in approximately 46 seconds. Upon removal of the circuit assemble, no fluorochemical residue was observed, but clean substantial reflow of the solder was observed and the assembly comprising the surface mounted device and printed circuit board were firmly affixed by the operation of the solder.

The novel compositions of matter of the present invention have particularly relevant utility in vapor phase soldering wherein components to be soldered are immersed in the vapor of the boiling compositions, the heat of vaporization of the vapor condensing on the solder components melts the solder to reflow it and the reflow and subsequent cooling by withdrawal from the vapor bath affect the soldering of components to one another. These techniques are set forth in U.S. Pat. No. Re. 30,399 and U.S. Pat. No. 4,549,686, the later of which discloses perfluorophenanthrene (perfluoroperhydrophenanthrene), both of which U.S. patents are hereby incorporated herein by reference. In the methods of the present invention the vapor bath is comprised of the various perfluorobutyldecalins or mixtures thereof, including mixtures such as perfluorobutyldecalin and perfluorophenanthrene (perfluoroperhydrophenanthrene).

The present invention has been described with reference to several preferred embodiments. However, the scope of the invention should be ascertained from the claims which follow.

I claim:

1. In a method of soldering wherein a component to be soldered is immersed in a vapor bath to melt the solder, and the component is then withdrawn from the vapor bath, the improvement comprising that the vapor bath is composed substantially of a compound of the formula:

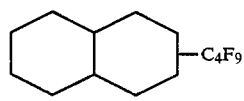

wherein the carbon rings are fully fluorinated, or mixtures thereof.

2. The method of claim 1 wherein the vapor bath further contains perfluorophenanthrene.

3. The method of claim 1 wherein the compound has the formula:

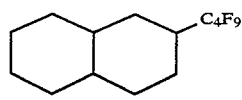

4. The method of claim 1 wherein the compound has the formula:

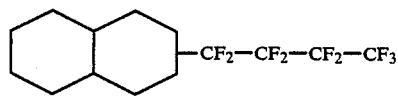

5. The method of claim 1 wherein the compound has the formula:

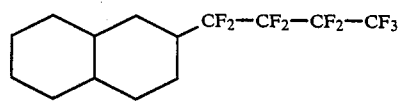

6. The method of claim 1 wherein the compound has the formula:

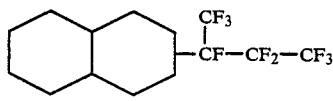

7. The method of claim 1 wherein the compound has the formula:

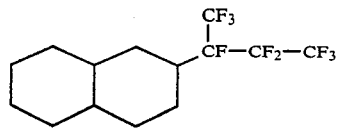

8. The method of claim 1 wherein the compound has the formula:

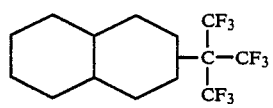

9. The method of claim 1 wherein the compound has the formula:

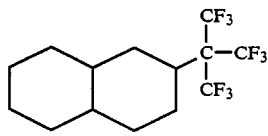

10. The method of claim 1 wherein the compound has the formula:

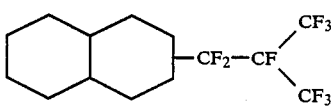

11. The method of claim 1 wherein the compound has the formula:

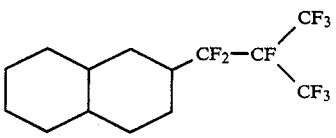

* * * * *